United States Patent [19]

Lin et al.

[11] Patent Number: 4,600,573

[45] Date of Patent: Jul. 15, 1986

[54] COMPOSITIONS AND METHOD FOR ALLEVIATING THE TOXIC EFFECTS OF 1,3-BIS(2-CHLOROETHYL)-1-NITROSOUREA

[75] Inventors: Tai-Shun Lin, North Haven; William H. Prusoff, Branford, both of Conn.

[73] Assignee: Research Corporation, New York, N.Y.

[21] Appl. No.: 719,397

[22] Filed: Apr. 3, 1985

Related U.S. Application Data

[63] Continuation-in-part of Ser. No. 458,334, Jan. 17, 1983, abandoned.

[51] Int. Cl.⁴ .............................................. A61K 31/70
[52] U.S. Cl. ........................................ 424/10; 514/50; 514/922
[58] Field of Search ..................... 424/10; 514/50, 922

[56] References Cited

PUBLICATIONS

Chemical Abstracts 95:17758n (1981).
Carter et al., Chemotherapy of cancer, 2nd ed., 1981, pp. 99 and 100, John Wiley & Sons, N.Y., N.Y.

*Primary Examiner*—Jerome D. Goldberg
*Attorney, Agent, or Firm*—Scully, Scott, Murphy & Presser

[57] ABSTRACT

This disclosure describes the preparation of therapeutically effective compositions of matter containing a nucleoside such as thymidine and 1,3-bis(2-chloroethyl)-1-nitrosourea (BCNU) which are useful in inhibiting the growth of transplanted tumors in mammals.

2 Claims, 2 Drawing Figures

COMPOSITIONS AND METHOD FOR ALLEVIATING THE TOXIC EFFECTS OF 1,3-BIS(2-CHLOROETHYL)-1-NITROSOUREA

CROSS REFERENCE TO RELATED APPLICATION

This application is a continuation-in-part of copending application Ser. No. 458,334, filed Jan. 17, 1983, now abandoned.

BRIEF SUMMARY OF THE INVENTION

This invention relates to novel compositions of matter and to a method for the treatment of cancer. More particularly, the present invention relates to a composition of matter comprising 1,3-bis(2-chloroethyl)-1-nitrosourea (BCNU) and thymidine (TdR) and/or deoxycytidine (CdR) and/or uridine (UR) useful in inducing regression of leukemia and/or inhibiting growth of tumors in mammals.

DETAILED DESCRIPTION OF THE INVENTION

Halogenated alkyl nitrosoureas have long been known as antineoplastic agents. The best known of the class is 1,3-bis(2-chloroethyl)-1-nitrosourea (BCNU) which has been used clinically. Unfortunately, the compound is toxic not only to neoplastic cells but also to normal cells. For this compound to be effective as an anticancer drug, it is necessary for such use to be below a specific minimum dosage, that is, below 40 milligrams per kilogram of body weight as the toxicity of BCNU is too high. The most consistent organic toxicities of this drug involve bone marrow, lymphoid tissue, kidneys, lungs, liver and the gastrointestinal tract. The art, therefore, has long sought the useful properties of this nitrosourea drug but without the undesirable side effects, or at least, in which the undesirable side effects can be controlled.

The present invention is based upon the discovery that the administration of thymidine to a subject permits the reduction of the dosage of BCNU below the critical 40 milligrams per kilogram dose level.

The thymidine is employed in an amount below that at which is has any observable antitumor activity. The net effect appears to be that the subject derives the beneficial effects of the antineoplastic activity of BCNU, but without necessarily encountering the toxic effects normally produced by treatment with BCNU. Since the clinical use of BCNU is limited by dose-related toxicity, the potential for use of a lower dose of BCNU to get the same efficacy would be of great value.

The beneficial effects of this novel combination of drugs have been observed in the control of tumors in mammals specifically L1210 leukemia in tumor-bearing mice, wherein the percent of survivors has been dramatically increased by the novel combination of drugs employed herein. As indicated earlier, it is also within the scope of the present invention to employ deoxycytidine (CdR) and/or uridine (UR) in lieu of thymidine to reduce the toxic effect of BCNU.

BRIEF DESCRIPTION OF THE DRAWING

The attached drawings, FIGS. 1 and 2, clearly show the dramatic increase in the number of mice surviving L1210 leukemia when treated with varying amounts of BCNU and two grams of thymidine (TdR) per kilogram of body weight.

DETAILED DESCRIPTION OF THE INVENTION

Figure 1:
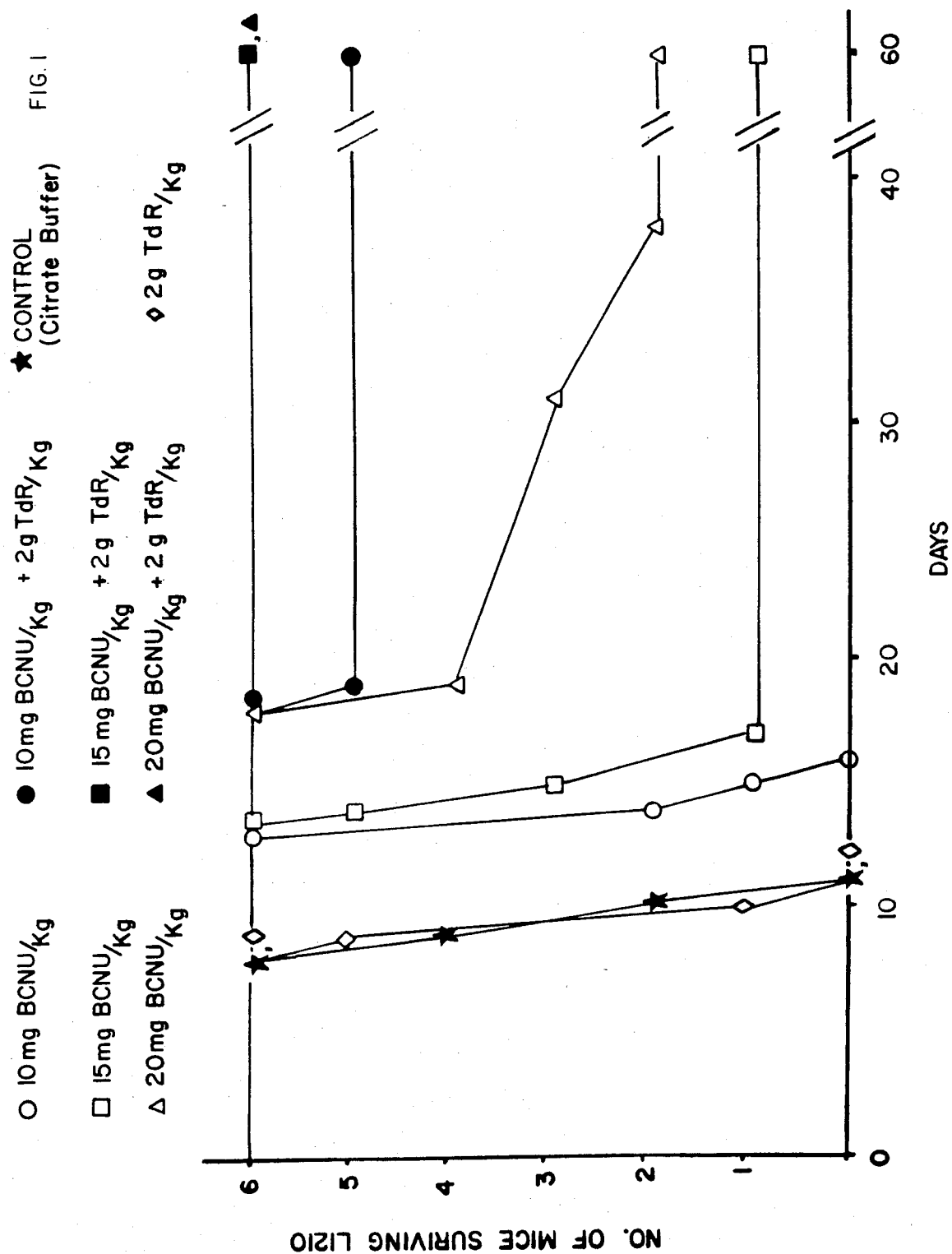
Figure 2:
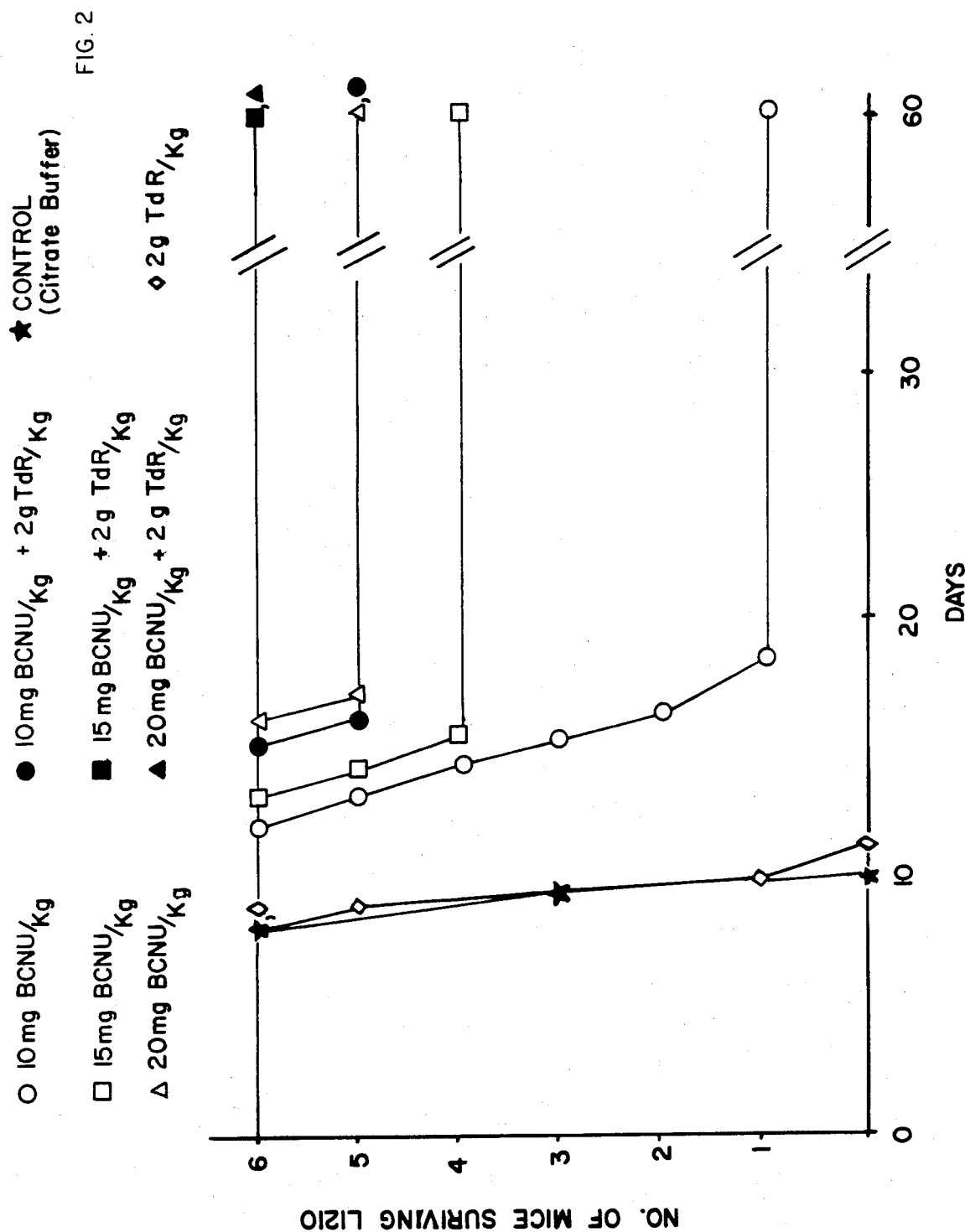

The compounds of this invention possess the property of inhibiting the growth of transplanted mouse tumors as established by the following test:

Lymphocytic leukemia L1210 test procedure

Mouse L1210 cells were maintained as suspension cultures in Fischer's medium supplemented with 10% horse serum at 37° C. in a humidified atmosphere of 5% $CO_2$-95% air. Under these conditions the generation time for L1210 cells is approximately 12 hours. The test compounds at the given concentration, were added to L1210 cells $2 \times 10^4$ cells/mL) which were in their exponential phase of growth. The increase in cell number of the drug-free culture (control), as well as that of the cultures supplemented with the test compound, was determined after 24, 58 and 72 hours of growth.

Transplantation of L1210 ascites cells was carried out by withdrawing peritoneal fluid from donor $CDF_1$ mice bearing 7-day growths. The suspension was centrifuged for 2 minutes (1600 g), the supernatant peritoneal fluid was decanted, and a 10-fold dilution with isotonic saline was made. The cell number was determined with a Coulter particle counter and the cell population was adjusted to $10^6$ cells/mL. One-tenth mL of the resulting cell suspension (containing approximately $10^5$ cells) was injected intraperitoneally into each animal. Drugs were administered once by intraperitoneal injection, 24 hours after tumor implantation. The test compounds were injected as a solution in 10% ethanol:90% 0.01 M citrate buffer (pH 4.0). All drugs were administered intraperitoneally in a volume of 0.25 mL. For any one experiment, animals were distributed into groups of six mice of comparable weight and maintained throughout the course of the experiment on a suitable diet and water "ad libitum". Controls given injections of a comparable volume of vehicle were included in each experiment. Mice were weighed during the course of the experiments, and the percentage change in body weight from onset to termination of therapy was used as an indication of drug toxicity. Determination of the sensitivity of ascitic neoplasms to these agents were based on the prolongation of survival time afforded by the drug treatments. The median survival time and the ratio of survival time for treated (T)/control (C) was calculated.

BCNU and thymidine were screened against $CDF_1$ female mice bearing L1210 leukemia according to the above NCI protocol. Three groups of mice with six mice in each group were inoculated with $1 \times 10^5$ L1210 murine leukemia cells. Starting 24 hours post inoculation, the first group of mice was injected with citrate buffer as the vehicle control and the other groups were injected with the stated quantities of BCNU and BCNU plus thymidine. The following survival rates shown in the table below were found at the end of sixty days.

TABLE 1

| DOSAGE | SURVIVORS % | |
|---|---|---|
| | Exp. 1 | Exp. 2 |
| 10 mg BCNU/kg + 2 g TdR/kg | 100 | 83 |
| 15 mg BCNU/kg + 2 g TdR/kg | 100 | 100 |
| 20 mg BCNU/kg + 2 g TdR/kg | 83 | 100 |
| 40 mg BCNU/kg + 2 g Tdr/kg | 0 | 0* |

TABLE 1-continued

| DOSAGE | SURVIVORS % | |
| --- | --- | --- |
| | Exp. 1 | Exp. 2 |
| 10 mg BCNU/kg | 0 | 17 |
| 15 mg BCNU/kg | 17 | 66 |
| 20 mg BCNU/kg | 33 | 83 |
| 40 mg BCNU/kg | | 66* |
| 2 g Tdr/kg | 0 | 0 |

*Non-tumor bearing mice

The above data clearly show the desirable effect of thymidine on the anticancer activity of BCNU in mice bearing L1210 leukemia, in terms of percent of survivors. The above data also clearly show that a lower level of BCNU plus thymidine is equivalent to a higher level of BCNU alone. However, in non-tumor bearing mice the co-administration of thymidine increases the toxicity of BCNU.

As indicated above, it is also within the scope of the present invention to employ deoxycytidine (CdR) and/or uridine (UR) in lieu of thymidine to potentiate the anticancer activity of BCNU.

The NCI protocol as described above was followed with citrate buffer as the control and the mice were infected with L1210 leukemia cells. The results are shown in the following table.

TABLE II

| DOSAGE | SURVIVORS % |
| --- | --- |
| 10 mg BCNU/Kg + 2 g CdR/kg | 83 |
| 10 mg BCNU/Kg + 2 g UR/kg | 50 |
| 10 mg BCNU/kg | 17 |
| Control | 0 |

The experiment was terminated on the 35th day due to infection in the mouse colony.

It is clear, however, from the foregoing table that other nucleosides in addition to thymidine enhance the anticancer activity of BCNU.

The active ingredients of the therapeutic compositions of the present invention induce regression of leukemia and/or inhibit growth of tumors in mammals (mouse) when administered in amounts ranging from about 10 mg to about 20 mg of BCNU per kilogram of body weight, and such dosage units are employed so that a total of from about 3 mg to about 60 mg per meter square or about 0.1 mg to about 5 mg/kg of the active compound for a subject of about 70 kg of body weight are administered in a 24-hour period. With respect to thymidine, expressed in terms of milligrams per kilogram of body weight for a subject of about 70 kg of body weight, this provides a dosage unit of from about 5 to about 150 mg/kg of body weight. The dosage regimen may be adjusted to provide the optimum therapeutic response. For example, several divided doses may be administered daily or the dose may be proportionally reduced as indicated by the exigencies of the therapeutic situation. A decided practical advantage is that the active compounds may be administered in any convenient manner such as by the oral, intraveneous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

It is expected that in normal use BCNU will be coadministered with the selected pyrimidine deoxyriboneucleoside or within a short period before administration, so that the active compound will perform its useful function and the inhibitor will protect the normal cells. The present preferred method of administration is parenteral.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micro-organisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

What is claimed is:

1. A pharmaceutical composition in dosage unit form comprising 1,3-bis(2-chloroethyl)-1-nitrosourea and thymidine in such concentration ratios as to provide dosage units containing from about 10 to 20 mg/kg of body weight of 1,3-bis(2-chloroethyl)-1-nitrosourea and about 2 g/kg of body weight of thymidine in association with a pharmaceutically acceptable carrier.

2. A method of alleviating the toxic effects of 1,3-bis(2-chloroethyl)-1-nitrosourea in a mammalian subject undergoing treatment with 1,3-bis(2-chloroethyl)-1-nitrosourea which comprises administering to said subject an effective amount of thymidine.

* * * * *